United States Patent [19]

Nakao et al.

[11] Patent Number: 4,965,264
[45] Date of Patent: Oct. 23, 1990

[54] THIENOCINNOLINE COMPOUNDS AND THEIR PHARMACEUTICAL USE

[75] Inventors: Toru Nakao; Kenji Morita; Masao Hisadome; Shuzo Takehara, all of Nakatsu, Japan

[73] Assignee: Yoshitomi Pharmaceutical Industries, Ltd., Osaka, Japan

[21] Appl. No.: 320,267

[22] PCT Filed: Mar. 17, 1988

[86] PCT No.: PCT/JP88/00290
§ 371 Date: Nov. 18, 1988
§ 102(e) Date: Nov. 18, 1988

[87] PCT Pub. No.: WO88/07533
PCT Pub. Date: Oct. 6, 1988

[30] Foreign Application Priority Data

Mar. 25, 1987 [JP] Japan ............... 62-70838

[51] Int. Cl.$^5$ .............. A61K 31/50; C07D 495/04
[52] U.S. Cl. .................. 514/248; 544/234; 549/32
[58] Field of Search ............... 544/234; 514/248

[56] References Cited

U.S. PATENT DOCUMENTS 4,701,453 10/1987 Sircar et al. ............ 544/234
4,843,075 6/1989 Nakao et al. ............ 514/248
4,849,421 7/1989 Nakao et al. ............ 514/248

FOREIGN PATENT DOCUMENTS 45754 9/1982 Japan .
45755 9/1982 Japan .
6278 1/1989 Japan ............... 544/234
2185977 8/1987 United Kingdom .

OTHER PUBLICATIONS

Derwent Abstract for JP 64/6278 (1/10/89).

Primary Examiner—Mukund J. Shah
Assistant Examiner—F. Bernhardt
Attorney, Agent, or Firm—Wenderoth, Lind & Ponack

[57] ABSTRACT

A thienocinnoline compound of the general formula

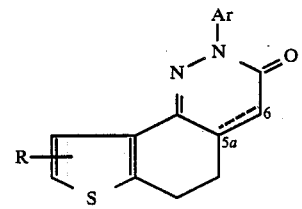

wherein R stands for hydrogen, a halogen or a lower alkyl, Ar stands for an aryl, a heteroaryl, or an aryl or a heteroaryl having as a substituent at least a halogen, a lower alkyl, a lower alkoxy, nitro, amino, hydroxy, trifluoromethyl and/or a lower alkanoylamino; and the bond≈between 5a-position and 6-position represents a single bond or a double bond, which is useful as an antianxiety agent, amnesia-treating drug, a brain function-activating drug, an antidementiac drug or a potentiating agent of biological protection.

3 Claims, No Drawings

THIENOCINNOLINE COMPOUNDS AND THEIR PHARMACEUTICAL USE

TECHNICAL FIELD

This invention relates to moriel thienocinnoline compounds and their pharmaceutical use.

BACKGROUND ART

Benzodiazepine (BZP) derivatives represented by diazepam have been used for a long time as an antianxiety drug or a therapeutic medicine for sleep disturbance. Recent pharmacological studies have shown that there exist receptors which exhibit a specific affinity for BZP derivatives in the central nervous system [Science, vol. 198, 849 (1977)]. In the studies and researches conducted subsequently, there have been investigated and developed not only BZP derivatives but also compounds which have structures different from BZP but exhibit a high affinity for BZP receptors and a BZP-like action (BZP agonist), compounds which exhibit a high affinity for BZP receptors but exhibit a pharmacological action reverse to BZP (BZP inverse-agonist), and compounds which exhibit a high affinity for BZP receptors but nevertheless exhibit no pharmacological activity themselves and rather show an antagonistic action against the action of the agonist or the inverseagonist (BZP antagonist) [Advance in Drug Research, vol. 14, 165 (1985)].

Since BZP derivatives which are used as an antianxiety drug have a sedative action, a muscle-relaxing action and an anticonvulsive action in addition to an anti-anxiety action, they often cause troubles in terms of side effects such as dizziness and sleepiness. Thus, research on non-BZP types of compounds with the object of developing selective antianxiety drugs with less side effects is thriving. Nevertheless, satisfactory compounds have not yet been found.

Also, in recent years, amnesia-inducing actions by BZP agonists were found [Nature, vol. 321, 864 (1986)], and there have been reports suggesting the possibility that BZP-antagonists exhibiting an antagonistic action against the amnesic actions induced by BZP agonists and BZP-inverse-agonists exhibiting an action reverse to the amnesic actions by BZP agonists are usable as brain-function activating drugs. [Trends in Neurosciences, vol. 11, 13 (1988)].

In the meantime, in the specification of U.S. Pat. No. 4,602,019 there are disclosed compounds such as 2,4,4a,5-tetra-hydro-7-(1H-imidazol-1-yl)-3H-indeno[1,2-c]pyridazin-3-one having a cardiac action and an antihypertensive action. The Journal of Medicinal Chemistry, vol. 24, 830 (1981) discloses compounds such as 2-(4-chlorophenyl)benzothiopyrano-[4,3-pyrazol-3-one possessing an immune-supressing action.

DISCLOSURE OF INVENTION

The present inventors have conducted intensive studies for the purpose of developing BZP-agonists, BZP-inverse-agonists or BZP-antagonists having a non-BZP-nucleus which are useful pharmaceuticals.

It has been found that the above-mentioned purpose can be attained according to the present invention described hereinafter.

That is, the first aspect of the invention is to provide thienocinnoline compounds of the general formula

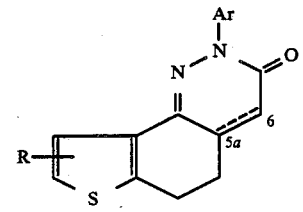

wherein R stands for hydrogen, a halogen or a lower alkyl, Ar stands for an aryl, a heteroaryl, or an aryl or a heteroaryl having as a substituent at least a halogen, a lower alkyl, a lower alkoxy, nitro, amino, hydroxy, trifluoromethyl and/or a lower alkanoylamino; and the bond ===== between 5a-position and 6-position represents a single bond or a double bond.

The second aspect of the invention is to provide pharmaceutical compositions comprising a thienocinnoline compound of the above general formula (I).

The symbols of the general formula (I) and each of the below-mentioned general formulae are defined in detail below. The halogen represents chlorine, bromine, fluorine or the like; the lower alkyl represents an alkyl having 1 to 4 carbon atom(s) such as methyl, ethyl, propyl, isopropyl, butyl, isobutyl or tert-butyl; the lower alkoxy represents an alkoxy having 1 to 4 carbon atom(s) such as methoxy, ethoxy, propoxy, isopropoxy butoxy, isobutoxy or tertbutoxy; the lower alkanoylamino represents an alkanoylamino having 2 to 5 carbon atoms such as acetylamino, propionylamino, butyrylamino or pivaloylamino; the aryl represents phenyl, naphthyl or the liked; and the heteroaryl represents a 5- or 6-membered ring or its fused ring containing 1 to 3 (preferably 1 or 2) hetero atom(s) (e.g. nitrogen, oxygen, sulfur) in the ring such as 2-, 3- or 4-pyridyl, 2- or 3-thienyl, 3- or 4-pyrazolyl, 1- or 2-imidazolyl, 2-, 4- or 5-pyrimidinyl, 3-, 4- or 5-pyridazinyl or 2-, 4- or 5-benzimidazolyl.

The compounds of the general formula (I) can be produced by subjecting to ring-closure reaction a compound of the formula

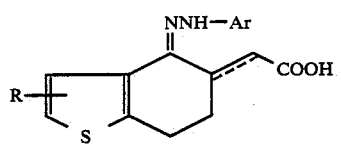

wherein each of the symbols is as defined above, which can be obtained by reacting a compound of the general formula

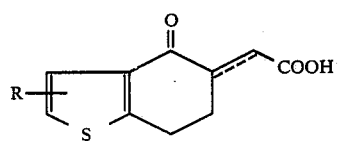

wherein R is as defined above, with a hydrazine derivative of the general formula

wherein Ar is defined as above or its acid addition salt.

The reactions proceed by heating under reflux in a suitable solvent, for example, an alcohol solvent such as methanol, ethanol or propanol for 5 to 20 hours to yield the compound of the formula (I) and the compound of the formula (IV).

In case an acid addition salt of the hydrazine derivative of the general formula (III) is employed, the reaction is conducted in the presence of an acid scavenger (sodium acetate, potassium acetate, sodium bicarbonate, sodium carbonate, potassium carbonate, pyridine, triethylamine, etc.).

When the compound of the general formula (IV) is obtained in the above reaction, the compound of the general formula (I) can be produced by heating the obtained compound of the general formula (IV) under reflux in acetic acid for 5-10 hours.

The compound of the general formula (I) wherein the bond between 5a-position and 6-position is a double bond can be synthesized also by adding bromine in an amount of 1-1.5 times mol dropwise to the corresponding compound of the general formula (I) wherein the bond between 5a-position and 6-position is a single bond, in acetic acid as the solvent at 20°-60° C. [Journal of Medicinal Chemistry, vol. 14, 262 (1971)], or by reacting the compound of the general formula (I) wherein the bond between 5a-position and 6-position is a single bond with sodium-m-nitrobenzenesulfonate (Bachmann method, United Kingdom Pat. No. 1168291).

The compounds of the general formula (I) which can be produced in the above-mentioned manner can be isolated and purified by a conventional method such as column chromatography or recrystallization.

The compounds of the (!general formula (II) of this invention are novel compounds which have not been described in any literature. The compounds can be produced by, for example, converting the corresponding compounds of the general formula

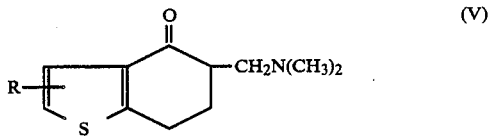

(V)

wherein R is as defined above, or their acid addition salts to their quaternary ammonium compounds by adding methyl iodide to the compounds of the general formula (V) or their acid addition salts in acetone and retaining the mixture at room temperature for 2-5 hours, followed by converting the quaternary ammonium compounds to the corresponding cyano compounds of the general formula

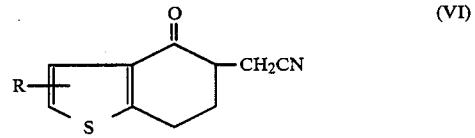

(VI)

wherein R is as defined above, by adding potassium cyanide or sodium cyanide to the quaternary ammonium compounds in an aqueous methanol and reacting the mixture at 30°-50° C. for 4-10 hours, followed by adding the thus-obtained compounds of the general formula (VI) to acetic acid and conc. hydrochloric acid and heating the mixture under reflux for 5-12 hours.

For reference sake, representative examples of the compounds of the general formula (II) are indicated with their melting points below.

4-Oxo-4,5,6,7-tetrahydrobenzo[b]thiophene-5-acetic acid, m.p. 118°-120° C.

2-Bromo-4-oxo-4,5,6,7-tetrahydrobenzo[b]thiophene-5-acetic acid, m.p. 134°-136° C.

2-Methyl-4-oxo-4,5,6,7-tetrahydrobenzo[b]thiophene-5-acetic acid, m.p. 117°-122° C.

The preparation of some of the esters of the compounds of the general formula (II) are reported by S. Kukolja et al. in Journal of Medicinal Chemistry, vol. 28, 1896 (1985).

The compounds of the general formula (I) exhibit a high affinity of $10^{-7}-10^{-9}M$ to BZP receptors and have an antagonistic action against chemical convulsants such as bicuculline and pentylenetetrazole. They also exhibit an inhibitory action against amnesia induced by electro-convulsive shock.

Furthermore, they exhibit pharmacological actions such as potentiating actions of leukocyte phagocytosis, potentiating actions of macrophage-phagocytosis and protective actions against infection.

The pharmacological actions of the compounds of the present invention are shown with the experimental methods therefor below.

EXPERIMENTAL EXAMPLE 1

Displacement ability for Benzodiazepine

The experiment for specific affinity to benzodiazepine receptors was carried out in accordance with the method described in Life Science, vol. 20, 2101 (1977).

The crude cyhaptosome fraction was isolated from the cerebral cortex of male Wistar rats aged 9-10 weeks, and was suspended in 50 mM Tris-hydrochloric acid buffer solution (pH 7.4) containing 120 mM sodium chloride and 5 mM potassium chloride. These suspensions were used for the experiment.

The test compounds in several different concentrations and tritiated diazepam (in final concentration of 2 nM) were added to the synaptosome suspensions, and the mixtures were incubated at 0° C. for 20 minutes. These suspensions were filtered with Whatman GF/B glassfiber filters. After the filters were washed with the above-mentioned buffer solution, the radioactivity left on the filters was measured with the use of a liquid scintillation counter.

Specific binding was determined by subtracting binding in the presence of $10^{-6}M$ unlabeled diazepam from total binding.

According to the foregoing experimental method, the binding force to benzodiazepine receptors of the compound of the present invention is evaluated from its displacement ability for tritiated diazepam at its binding site, which is represented by Ki value (nM).

The results of the experiment are shown in Table 1.

TABLE 1

| Test compound (Example No.) | Affinity to BZP Receptors, Ki (nM) |
|---|---|
| 3 | 280 |
| 4 | 30 |
| 5 | 18 |
| 6 | 12 |
| 7 | 60 |

TABLE 1-continued

| Test compound (Example No.) | Affinity to BZP Receptors, Ki (nM) |
|---|---|
| 9 | 12 |
| 10 | 7 |
| 11 | 4.5 |
| 14 | 5.1 |
| 24 | 10 |

EXPERIMENTAL EXAMPLE 2

Anti-Bicuculline Action

The anti-bicuculline action test was carried out in accordance with the method described in Life Science, vol. 21, 1779 (1977).

Male ddY mice weighing 20-28 g, 7-14 animals per group, were used. One hour after the oral administration of the test compounds, (+) bicuculline was intravenously administered at the dosage of 0.6 mg/kg, and 50% effective concentration ($ED_{50}$) was estimated by examining whether the tonic convulsion within 5 minutes was caused or not. The result was that the $ED_{50}$ values of the compounds of Examples 6, 10 and 24 were 50-100 mg.

EXPERIMENTAL EXAMPLE 3

Action on Experimental Amnesia

The experiment was carried out in accordance with the method described by Sara in Psychopharmacologia, vol. 36, 59 (1974).

Male ddY mice weighing 23-26 g, 20 animals per group, were used, and a step-through passive avoidance reflex practicing box consisting of illuminated chamber and dark chamber was used as the experimental apparatus. As the acquisition trial of passive avoidance reflex, the animals were placed in the illuminated chamber and then allowed to enter the dark one. As soon as the animals entered the dark chamber, footshock was applied to the mouse. Experimental amnesia was caused by applying electroconvulsive shock [ECS]soon after the acquisition trial. As the experimental trial, the animals were placed in the illuminated chamber three hours after the acquisition trial, and the time which the animals took to enter the dark chamber (latency) was measured until 600 seconds. The test compounds were administered intraperitoneally (i.p.) immediately after the application of ECS.

For the evaluation of the effects, antagonistic actions against the reduction in latency, caused by the application of ESC were examined. Measured was the minimum effective dose (MED) at which a significant antagonistic action was exhibited in the mouse treated with the test compounds as compared with controls. The results are summarized in Table 2.

TABLE 2

| Test compound (Example No.) | Anti-amnesia Action MED (mg/kg, ip) |
|---|---|
| 3 | 0.1 |
| 4 | 0.5 |
| 5 | 0.25 |
| 7 | <0.5 |
| 9 | 0.5 |
| 14 | 0.25 |

EXPERIMENTAL EXAMPLE 4

Action on Leukocyte-phagocytosis

The experiment was performed in accordance with the method by Stossel et al. [Journal of Clinical Investigation, vol. 51, 615 (1972)].

ICR mice weighing 30-35 g were intraperitoneally administered with glycogen. Three hours later, the leukocytes in the abdominal cavity were collected. A leukocyte suspension of $5 \times 10^6$ cells/ml was prepared and the test compound was added to 200 µl of the cell suspension, followed by further addition of 100 µl of mouse serum and 100 µl of dead yeast ($1 \times 10^8$ particles/ml) thereto. The mixture was incubated at 37° C. for 20 minutes. By observing more than 200 leukocytes in the reaction mixture under a microscope (400 magnifications), the number of the leukocytes which had phagocytosed at least one dead yeast was counted. The ratio of the number of phagocytic leukocytes treated with 0.1 µM of the test compounds relative to that of phagocytic leukocytes of controls was estimated. The potentiating actions on phagocytosis of the compounds of Examples 1 and 9 were 160% and 158% respectively.

EXPERIMENTAL EXAMPLE 5

Action on Macrophage-phagocytosis

Casein sodium was intraperitoneally administered to rats. Three to four days later, peritoneal macrophages were collected. The phagocytosis was examined, and the relative ratio of phagocytic macrophages of the rat treated with 0.1 µM of the test compound was calculated in the same manner as Experimental Example 4. The potentiating actions on phagocytosis of the compounds of Examples 2, 8 and 10 were 146%, 167% and 148% respectively.

EXPERIMENTAL EXAMPLE 6

Infection-protective Action

Cyclophosphamide was intraperitoneally administered to male ICR mice (weighing 23-27 g, aged 5 weeks) at the dosage of 200 mg/kg. Four days later, $1 \times 10^{-8}$ CFU of E. coli 0-111 strain was subcutaneously inoculated into the mice (Controls). The test compounds (3 mg/kg) were orally administered to the mice for 3 days from the following day of the administration of cyclophosphamide. The survival rate of the treated mice relative to controls 7 days after the inoculation of E. coli was compared. Thus, the compounds of Examples 2, 8 and 11 exhibited significant increasing effects on survival rate.

As apparent from the foregoing various pharmacological studies, including experiments, the compounds (I) of the present invention have a high affinity for BZP receptors and exhibit an antagonistic action against chemical convulsion-inducing agents such as bicuculline and pentylenetetrazole, whereas they influence to a small extent somatic functions such as muscle-relaxing actions. Thus, they are useful as an antianxiety agent. Also, since they possess an inhibitory action on amnesia induced by electroconvulsive shock, they are useful as an amnesia-treating drugs, brain function-activating drugs and antidementiac drugs. They are also of value as an antidote for excessive administration of or toxicosis by existent antianxiety drugs such as diazepam. Besides, in view of the fact that they have leukocyte-phagocytosis-potentiating actions, macrophagephagocytosis-potentiating actions, infection-protective actions and other pharmacological actions, they are useful as a potentiating agent of biological protection.

When the compounds of the general formula (I) are used as pharmaceuticals, a therapeutically effective amount of the compounds and adequate pharmacologically acceptable additives such as excipient, carrier, diluent and so on are mixed and formulated into a form such as tablets, capsules, granules, syrups, injectable solutions, suppositories, dispersible powders or the like and are administered in a form mentioned above. The dosage, for example, in the case of oral administration, is generally about 5–500 mg daily per adult, which is administered once a day or in divided doses several times a day.

EXAMPLES

This invention is more specifically described below with working examples, which are not to be construed as limitative.

EXAMPLE 1

4-Oxo-4,5,6,7-tetrahydrobenzo[b]thiophene-5-acetic acid (3.7 g) and 1.9 ml of phenylhydrazine are dissolved in 50 ml of butanol. After the mixture is stirred at an outside temperature of 90° to 100° C. for 3 hours, the solvent is distilled off. The residue is purified by column chromatography to give crude crystals, which are recrystallized from ethanol to afford 1.2 g of 8-phenyl-4,5,5a,6,7,8-hexahydrothieno[2,3h]cinnolin-7-one, m.p. 117°–119° C.

EXAMPLE 2

Using 4-chlorophenylhydrazine instead of phenylhydrazine as used in Example 1, the reaction and procedure are conducted by the same method as that of Example 1 to yield 8-(4-chlorophenyl)4,5,5a,6,7,8-hexahydrothieno[2,3-h]cinnolin-7-one, m.p. 169°–171° C.

EXAMPLE 3

The reaction and procedure are conducted in the same manner as that of Example 1 using 2-hydrazinopyridine in place of phenylhydrazine as used in Example 1 to give 8-(2-pyridyl)4,5,5a,6,7,8-hexahydrothieno[2,3-h]cinnolin-7-one, m.p. 135°–136° C.

EXAMPLE 4

The reaction and procedure are conducted by the same method as that of Example 1 using 2-bromo-4-oxo-4,5,6,7-tetrahydrobenzo[thiophene-5-acetic acid instead of 4-oxo-4,5,6,7-tetrahydrobenzo[thiophene-5-acetic acid as used in Example 1 to give 2-bromo-8-phenyl-4,5,5a,6,7,8-hexahydrothieno[2,3-h]-cinnolin-7-one, m.p. 131°–133° C.

EXAMPLE 5

By following the reaction and procedure conducted by the same method as that of Example 1 using 2-methyl-4-oxo-4,5,6,7tetrahydrobenzo[b]thiophene-5-acetic acid in place of 4-oxo4,5,6,7-tetrahydrobenzo[b]thiophene-5-acetic acid as used in Example 1 give 2-methyl-8-phenyl-4,5,5a,6,7,8-hexahydrothieno[2,3-h]cinnolin-7-one, m.p. 106°–108° C is produced.

EXAMPLE 6

By following the reaction and procedure conducted by the same method as that of Example 1 using 2-bromo-4-oxo-4,5,6,7-tetrahydrobenzo[b]thiophene-5-acetic acid instead of 4-oxo4,5,6,7-tetrahydrobenzo[b]thiophene-5-acetic acid as used in Example 1 and 4-chlorophenylhydrazine instead of phenylhydrazine, 2-bromo-8-(4-chlorophenyl)-4,5,5a,6,7,8-hexahydrothieno[2,3-h]cinnolin-7-one m.p. 115°–117° C. is produced.

EXAMPLE 7

By conducting the reaction and procedure by the same method as that of Example 1 using 2-bromo-4-oxo-4,5,6,7-tetrahydrobenzo[b]thiophene-5-acetic acid instead of 4-oxo4,5,6,7-tetrahydrobenzo[b]thiophene-5-acetic acid as used in Example 1 and 2-hydrazinopyridine instead of phenylhydrazine as used in Example 1, 2-bromo-8-(2-pyridyl)-4,5,5a,6,7,8-hexahydrothieno[2,3-h]cinnolin-7-one, m.p. 138°–141° C., is produced.

EXAMPLE 8

In 50 ml of butanol are dissolved 3.0 g cf 4-oxo-4,5,6,7-tetrahydrobenzo[b]thiophene-5-acetic acid and 2.5 g of 4-methylphenylhydrazine hydrochloride, whereto 1.3 g of sodium acetate is added. The mixture is heated under reflux for 2 hours. After the solvent is distilled off, water is added thereto. The mixture is extracted with chloroform, washed with water and dried over anhydrous magnesium sulfate. The solvent is distilled off. The obtained crude crystals are purified by column chromatography, and recrystallized from ethanol to yield 2.3 g of 8-(4-methylphenyl)-4,5,5a,6,7,8-hexahydrothieno[2,3-h]cinnolin-7-one, m.p. 157°–160° C.

EXAMPLE 9

The reaction and procedure are conducted by the same method as that of Example 8 using 4-methoxyphenylhydrazine hydrochloride in place of 4-methylphenylhydaazine hydrochloride as used in Example 8 to afford 8-(4-methoxyphenyl)4,5,5a,6,7,8-hexahydrothieno[2,3-h]cinnolin-7-one, m.p. 190°–192° C.

EXAMPLE 10

By following the reaction and procedure by the same method as that of Example 8 using 2-bromo-4-oxo-4,5,6,7-tetrahydrobenzo[b]thiophene-5-acetic acid in place of 4-oxo-4,5,6,7-tetrahydrobenzo[b]thiophene-5-acetic acid as used in Example 8, 2-bromo-8-(4-methylphenyl)-4,5,5a,6,7,8-hexahydrothieno[2,3-h]cinnolin-7-one, m.p. 142°–144° C., is produced.

EXAMPLE 11

By following the reaction and procedure by the same method as that of Example 8 using 2-bromo-4-oxo-4,5,6,7-tetrahydrobenzo[b]thiophene-5-acetic acid instead of 4-oxo-4,5,6,7-tetrahydrobenzo[b]thiophene-5-acetic acid as used in Example 8 and 4-methoxyphenylhydrazine hydrochloride instead of 4-methylphenylhydrazine hydrochloride as used in Example 8, 2-bromo-8-(4-methoxyphenyl)-4,5,5a,6,7,8-hehahydrothieno[2,3-h]cinnolin-7-one, m.p. 155°–156° C., is produced.

EXAMPLE 12

By following the reaction and procedure by the same method as that of Example 8 using 2-methyl-4-oxo-4,5,6,7-tetrahydrobenzo[b]thiophene-5-acetic acid instead of 4-oxo4,5,6,7-tetrahydrobenzo[b]thiophene-5-acetic acid as used in Example 8 and 4-chlorophenylhydrazine hydrochloride instead of 4-methylphenylhydrazine hydrochloride, 2-methyl-8-(4-chlorophenyl)-

4,5,5a,6,7,8-hexahydrothieno[2,3-h]cinnolin-7one, m.p. 137°-139° C., is obtained.

The following compounds can be obtained in the same manner as in the above examples.

EXAMPLE 13

2-Methyl-8-(2-pyridyl)-4,5,5a,6,7,8-hexatydrothieno[2,3-h]cinnolin-7-one, m.p. 143°-145° C.

EXAMPLE 14

2-Methyl-8-(4-methoxyphenyl)-4,5,5a,6,7,8-hexahydrothieno[2,3-h]cinnolin-7-one, m.p. 133°-135° C.

EXAMPLE 15

8-(4-Nitrophenyl)-4,5,5a,6,7,8-hexahydrothieno[2,3-h] cinnolin-7-one.

EXAMPLE 16

8-(3-Trifluoromethylphenyl)-4,5,5a,6,7,8-hexahydrothieno[2,3-h]cinnolin-7-one.

EXAMPLE 17

8-(4-Aminophenyl)-4,5,5a,6,7,8-hexahydrothieno[2,3-h]cinnolin-7-one.

EXAMPLE 18

8-(4-Acetylaminophenyl)-4,5,5a,6,7,8-hexahydrothieno[2,3-h]cinnolin-7-one.

EXAMPLE 19

8-(4-Hydroxyphenyl)-4,5,5a,6,7,8-hexahydrothieno[2,3-cinnolin-7-one, m.p. 268°-269° C.

EXAMPLE 20

2-Methyl-8-(3-methylphenyl)-4,5,5a,6,7,8-hexahydrothieno[2,3-h]cinnolin-7-one.

EXAMPLE 21

2-Methyl-8-(4-nitrophenyl)-4,5,5a,6,7,8-hexahydrothieno[2,3-h]cinnolin-7-one.

EXAMPLE 22

2-Methyl-8-(4-acetylaminophenyl)-4,5,5a,6,7,8-hexahydrothieno[2,3-h]cinnolin-7-one.

EXAMPLE 23

2-Methyl-8-(4-hydroxyphenyl)-4,5,5a,6,7,8-hexahydrothieno[2,3-h]cinnolin-7-one.

EXAMPLE 24

2-Methyl-8-(4-methylphenyl)-4,5,5a,6,7,8-hexahydrothieno[2,3-h]cinnolin-7-one, m.p. 120°-122° C.

EXAMPLE 25

8-(3-Methoxyphenyl)-4,5,5a,6,7,8-hexahydrothieno[2,3-h]cinnolin-7-one, m.p. 135°-137° C.

EXAMPLE 26

8-(2-Methoxyphenyl)-4,5,5a,6,7,8-hexahydrothieno[2,3-h]cinnolin-7-one, m.p. 148°-150° C.

EXAMPLE 27

8-(4,6-Dimethyl-2-pyrimidinyl)-4,5,5a,6,7,8-hexahydrothieno[2,3-h]cinnolin-7-one, m.p. 230°-232° C.

EXAMPLE 28

8-(6-Chloro-3-pyridazinyl)-4,5,5a,6,7,8-hexahydrothieno[2,3-h]cinnolin-7-one, m.p. 263°-264° C. (decomposition).

EXAMPLE 29

8-(4-Methoxy-2-pyrimidinyl)-4,5,5a,6,7,8-hexahydrothieno[2,3-h]cinnolin-7-one.

EXAMPLE 30

In 50 ml of acetic acid is dissolved 1.6 g of 2-methyl8-(4-methylphenyl)-4,5,5a,6,7,8-hexahydrothieno[2,3-h]cinnolin-7-one as obtained in Example 24, and 0.2 ml of bromine is added to the solution while stirring at room temperature. The mixture is mixed at 80°-90° C. for 30 minutes. After the solvent is distilled off, the obtained crystals are purified by way of silica gel column chromatography, followed by recrystallization from isopropyl alcohol to give 0.8 g of 2-methyl-8-(4-methylphenyl)-4,5,7,8tetrahydrothieno[2,3-h]cinnolin-7-one, m.p. 160°-162° C.

EXAMPLE 31

Formulation Example

Tablets containing 10 mg of a compound of the general formula (I) are prepared in accordance with the following formulation.

| | |
|---|---|
| Compound of formula (I) | 10.0 mg |
| Lactose | 58.5 mg |
| Corn starch | 25.0 mg |
| Crystalline cellulose | 20.0 mg |
| Polyvinylpyrrolidone K-30 | 2.0 mg |
| Talc | 4.0 mg |
| Magnesium stearate | 0.5 mg |
| | 120.0 mg |

The compound of the formula (I) is pulverized by an atomizer into fine powders below 10 μ in average particle diameter, which are admixed with lactose, corn starch and crystalline cellulose sufficiently in a kneading machine, and further kneaded with polyvinylpyrrolidone paste. The kneaded mixture is passed through a sieve of 200 mesh, dried at 50° C. and passed through a sieve of 24 mesh. Talc and magnesium stearate are mixed therewith and the mixture is compressed into 120.0 mg tablets with a punch of 8 mm in diameter. These tablets are, if desired, subjected to sugar-coating or film-coating.

While the present invention has been adequately and sufficiently described in the foregoing specification, including examples, modifications within the spirit and scope of this invention are possible.

We claim:

1. A thienocinnoline compound of the formula

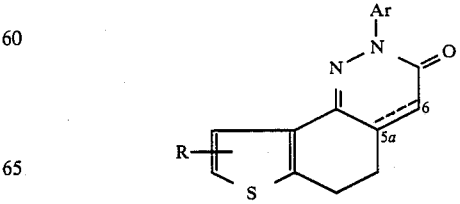

wherein R is hydrogen, a halogen or a lower alkyl;

Ar is a member selected from the group consisting of phenyl, naphthyl, pyridyl, thienyl, pyrazolyl, imidazolyl, pyrimidinyl, pyridazinyl and benzimidazolyl, which Ar is unsubstituted or substituted by 1 or 2 members selected from the group consisting of halogen, lower alkyl, lower alkoxy, nitro, amino, hydroxy, trifluoromethyl and lower alkanoylamino; and the bond ===== between the 5a-position and 6-position is a single bond or a double bond.

2. A compound selected from the group consisting of 8-(2-pyridyl)-4,5,5a,6,7,8-hexahydrothieno[2,3-h]cinnolin-7-one, 2-bromo-8-phenyl-4,5,5a,6,7,8-hexahydrothieno[2,3-h]cinnolin-7-one, -methyl-8-phenyl-4,5,5a,6,7,8-hexathydrothieno[2,3-h]cinnolin-7-one, -bromo-8-(4-chlorophenyl)-4,5,5a,6,7,8-hexahydrothieno[2,3-h]cinnolin-7-on -bromo-8-(2-pyridyl)-4,5,5a,6,7,8-hexahydrothieno[2,3-h]cinnolin-7-one, -(4-methoxyphenyl)-4,5,5a,6,7,8-hexahydrothieno[2,3-h]cinnolin-7-one, -bromo-8-(4-methylphenyl)-4,5,5a,6,7,8-hexahydrothieno[2,3-h]cinnolin-7-one -bromo-8-(4-methoxyphenyl)-4,5,5a,6,7,8-hexahydrothieno[2,3-h]cinnolin-7-one, 2-methyl-8-(4-methoxyphenyl)-4,5,5a,6,7,8-hexahydrothieno[2,3-h]cinnolin-7-one and 2-methyl-8-(4-mythylphenyl)-4,5,5a,6,7,8-hexahydrothieno [2,3-h]cinnolin-7-one.

3. A pharmaceutical composition for treating anxiety, amnesia or dementia, or for potentiating leukocyte or macrophage phagocytosis, comprising an effective amount of a compound as claimed in claim 1 or 2, and a pharmaceutically acceptable additive.

* * * * *